United States Patent [19]

Delavarenne et al.

[11] 4,335,050

[45] Jun. 15, 1982

[54] PROCESS FOR THE PREPARATION OF THE 5- AND 6-NITRO DERIVATIVES OF 1,2,3,4-TETRAHYDRO-ANTHRAQUINONE FROM 1,2,3,4,4A,9A-HEXAHYDRO-9,10-ANTHRACENE-DIONE

[75] Inventors: Serge Delavarenne, Francheville le Haut; Pierre Tellier, Sainte Foy les Lyon, both of France

[73] Assignee: PCUK Produits Chimiques Ugine Kuhlmann, Courbevoie, France

[21] Appl. No.: 80,030

[22] Filed: Sep. 28, 1979

[30] Foreign Application Priority Data

Oct. 17, 1978 [FR] France ................................. 78 29507

[51] Int. Cl.$^3$ ............................................. C07C 50/18
[52] U.S. Cl. .................................................. 260/369
[58] Field of Search ......................................... 260/369

[56] References Cited

U.S. PATENT DOCUMENTS

| 1,821,035 | 9/1931 | Schirmacher et al. | 260/369 |
| 3,962,288 | 6/1976 | Vaughan | 260/369 |

FOREIGN PATENT DOCUMENTS

| 502043 | 6/1930 | Fed. Rep. of Germany | 260/369 |
| 504646 | 7/1930 | Fed. Rep. of Germany | 260/369 |
| 603285 | 3/1960 | Italy | 260/369 |

*Primary Examiner*—Thomas A. Waltz
*Assistant Examiner*—Raymond K. Covington
*Attorney, Agent, or Firm*—Pennie & Edmonds

[57] ABSTRACT

Process for the preparation of the mononitro derivatives substituted in positions 5 or 6 of 1,2,3,4-tetrahydro-anthraquinone, which comprises nitrating 1,2,3,4,4a,9a-hexahydro-9,10-anthracene-dione by means of nitric acid or a mixture of nitric acid and sulfuric acid.

7 Claims, No Drawings

PROCESS FOR THE PREPARATION OF THE 5- AND 6-NITRO DERIVATIVES OF 1,2,3,4-TETRAHYDRO-ANTHRAQUINONE FROM 1,2,3,4,4A,9A-HEXAHYDRO-9,10-ANTHRACENE-DIONE

TECHNICAL FIELD

The present invention relates to the preparation of the mononitro derivatives substituted in positions 5 or 6 of 1,2,3,4-tetrahydro-anthraquinone by nitration of 1,2,3,4,4a,9a-hexahydro-9,10-anthracene-dione. These derivatives are intermediates which may be used in the preparation of mononitro derivatives in positions $\alpha$ and $\beta$ of anthraquinone.

BACKGROUND ART

The mononitro derivatives in positions $\alpha$ and $\beta$ of anthraquinone are important intermediates in the manufacture of dyestuffs. It is known that $\alpha$-nitroanthraquinone may be obtained by nitration of anthraquinone, but this reaction leads to the unavoidable formation of dinitro derivatives which first have to be eliminated in order to recover the desired anthraquinone. It is also known to prepare 2-nitro-1,4,4a,9a-tetrahydroanthraquinone by the nitration of 1,4,4a,9a-tetrahydro-anthraquinone as described in Japanese Pat. No. 77,108,429. However, this method does not result in a mononitro derivative capable of yielding the subsequent $\alpha$-nitro-anthraquinone.

DISCLOSURE OF THE INVENTION

Applicants have now found that it is possible to selectively obtain excellent yields of mono derivatives substituted in positions 5 and 6 of 1,2,3,4-tetrahydro-anthraquinone by nitration of 1,2,3,4,4a,9a-hexahydro-9,10-anthracene-dione. 5-nitro-1,2,3,4-tetrahydro-anthraquinone and 6-nitro-1,2,3,4-tetrahydro-anthraquinone are obtained in variable proportions according to the conditions of the reaction, the 5-nitro-compound being the preponderant product.

The 1,2,3,4,4a,9a-hexahydro-9-10-anthracenedione may be prepared according to the process of French Pat. No. 78,19466 wherein the process involves the hydrogenation of 1,4,4a,9a-tetrahydro-anthraquinone, the latter reactant being obtained from the Diels Alder reaction between 1,4-naphthoquinone and butadiene.

BEST MODE FOR CARRYING OUT THE INVENTION

The nitration of 1,2,3,4,4a,9a-hexahydro-9,10-anthracene-dione may be carried out in a mixture of sulfuric acid and nitric acid or in pure nitric acid. It is also possible to operate in the presence of a solvent which is inert under the conditions of the reaction. In the case where the nitration is carried out in a mixture of nitric acid and sulfuric acid, the concentration of the sulfuric acid should be greater than about 90%. Oleum can also be used. The concentration of the nitric acid depends on that of the sulfuric acid but it is preferably greater than 90% by weight. In the case where the nitration is carried out in nitric acid alone, the concentration of the nitric acid should be at least about 90% by weight and preferably at least about 98%.

The nitration may be carried out at a temperature between about 0° and about 50° C., preferably between about 0° and about 30° C.

The 5-nitro-1,2,3,4-tetrahydro-anthraquinone is much less soluble than the 6-nitro-1,2,3,4-tetrahydro-anthraquinone and it can thus also be more easily isolated in a pure state. When the nitration is effected in a mixture of sulfuric acid and nitric acid, the resulting 5-nitro-1,2,3,4-tetrahydro-anthraquinone is insoluble in the medium and can be isolated by simple filtration. In the case of a mixture of 5-nitro- and 6-nitro-1,2,3,4-tetrahydro-anthraquinones, it is easy to isolate the pure 5-nitro-1,2,3,4-tetrahydro-anthraquinone by recrystallization from a suitable solvent.

The following Examples illustrate a particularly preferred embodiment of the present invention without limiting its scope.

EXAMPLE 1

Into a 250 ml reactor provided with an agitator and containing 98.4 g of 96% sulfuric acid and 18.2 g of 100% nitric acid, there is introduced 21.4 g of 1,2,3,4,4a,9a-hexahydro-9,10-anthracene-dione over a period of 30 minutes and at a temperature of 5° C. The temperature is maintained for 3 hours at between 15° and 18° C. The product is then filtered and the precipitate is washed and dried, weighing 16 g. It consists of practically pure 5-nitro-1,2,3,4-tetrahydro-anthraquinone. The melting point of the product is 184°–185° C.

NMR spectrum (deuterated benzene at 60° C.):
 4 H methylene in positions 1 and 4, $\delta = 2.15$ ppm
 4 H methylene in positions 2 and 3, $\delta = 1.18$ ppm
 2 H aromatics in positions 7 and 8, $\delta = 6.93$ ppm
 1 H aromatic in position 6, $\delta = 7.83$ ppm
IR spectrum:
 $\delta NO_2$ at 1540 cm$^{-1}$
 $\gamma CO$ at 1660 cm$^{-1}$ A further 6.7 g of a product consisting principally of 6-nitro-1,2,3,4-tetrahydro-anthraquinone is collected by dilution of the filtrate.

NMR spectrum:
 4 H methylene in positions 1 and 4, $\delta = 2.25$ ppm
 4 H methylene in positions 2 and 3, $\delta = 1.22$ ppm
 2 H aromatics in positions 7 and 8, $\delta = 7.8$ ppm
 1 H aromatic in position 5, $\delta = 8.67$ ppm
IR spectrum:
 $\gamma NO_2$ at 1530 cm$^{-1}$
 $\gamma CO$ at 1650 cm$^{-1}$ The total yield is 88.3%

The 1,2,3,4,4a,9a-hexahydro-9,10-anthracenedione may be prepared as follows according to Example 1 of French Patent Application No. 78,19466:

Into a stainless steel autoclave provided with devices for heating and agitation, there is introduced 100 ml of toluene, 21.2 g of 1,4,4a,9a-tetrahydro-anthraquinone and 0.2 g of a catalyst consisted of palladium deposited on carbon, containing 5% palladium. The mixture is heated to 100° C. and hydrogen is introduced under a pressure of 30 bars. The reaction is continued for 4 hours while the pressure is maintained at between 20 and 30 bars. After cooling, 7 g of an insoluble product are separated by filtration, the product being in the form of green crystals melting at 206°–208° C. and of molecular mass 214, and of which the NMR and IR spectra show that litis 1,2,3,4-tetrahydro-9,10-anthracene-diol. By concentration of the filtrate there is obtained 14 g of a product melting at 80°–88° C. (M.P. of 89°–91° C. after recrystallization from hexane) which consists of practically pure 1,2,3,4,4a,9a-hexahydro-9,10-anthracene-dione.

EXAMPLE 2

10.7 g of 1,2,3,4,4a,9a-hexahydro-9,10-anthracenedione are slowly introduced into a reactor similar to that of Example 1, containing 63 g of 100% nitric acid. The temperature is maintained at 40° C. for a period of 4 hours, after which the reaction mixture is poured into a liter of water. The precipitate that is formed is washed ad dried, and weighs 11 g. Thin layer chromotography shows that it consists of a mixture of 5-nitro-1,2,3,4-tetrahydro-anthraquinone and 6-nitro-1,2,3,4-tetrahydro-anthraquinone. The yield is 85.6%.

EXAMPLE 3

107 g of 1,2,3,4,4a,9a-hexahydro-9,10-anthracenedione are slowly introduced—so as not to exceed a temperature of 10° C.—into a 1-liter reactor provided with an agitator and containing 630 g of 100% nitric acid. The mixture is maintained at 10° C. for a period of 6 hours, after which the resulting solution is poured into 3 liters of water at 0° C. The precipitate that is formed is collected, washed and dried and weighs 121 g. NMR analysis shows that it contains 80% of 5-nitro-1,2,3,4-tetrahydro-anthraquinone. The yield is 94.2%. On recrystallization of 110 g of the precipitate from perchlorethylene, 81 g of pure 5-nitro-1,2,3,4-tetrahydro-anthraquinone are obtained. The melting point is 185° C.

We claim:

1. A process for preparing mononitro derivatives substituted in positions 5 or 6 of 1,2,3,4-tetrahydroanthraquinone which comprises reacting 1,2,3,4,4a,9a-hexahydro-9,10-anthracenedione with nitric acid to simultaneously oxidize and nitrate 1,2,3,4,4a,9a-hexahydro-9,10-anthracene-dione to produce 5-nitro-1,2,3,4-tetrahydroanthraquinone and/or 6 nitro-1,2,3,4-tetrahydroanthraquinone.

2. A process according to claim 1 wherein the nitration is carried out in a mixture of nitric acid and sulfuric acid.

3. A process according to claim 2 wherein the concentration of the sulfuric acid is between about 70% and about 100% by weight.

4. A process according to claim 3 wherein the concentration of the sulfuric acid is greater than about 90% by weight.

5. A process according to claim 2 wherein the concentration of the nitric acid is between about 70% and about 100% by weight.

6. A process according to claim 5 wherein the concentration of the nitric acid is greater than about 90% by weight.

7. A process according to claim 1 wherein the nitration is carried out in pure nitric acid.

* * * * *

UNITED STATES PATENT AND TRADEMARK OFFICE
CERTIFICATE OF CORRECTION

PATENT NO. : 4,335,050
DATED : June 15, 1982
INVENTOR(S) : Serge Delavarenne and Pierre Tellier It is certified that error appears in the above—identified patent and that said Letters Patent is hereby corrected as shown below:

Column 1, line 35, reads "mono derivatives" should read --mono nitro derivatives--.

Column 2, line 34, reads "$\delta NO_2$" should read --$\gamma NO_2$--.

Column 2, line 64, reads "litis" should read --it is--.

Column 3, line 10, reads "ad" (first occurrence), should read --and--.

Signed and Sealed this

Twenty-fourth Day of August 1982

[SEAL]

Attest:

GERALD J. MOSSINGHOFF

Attesting Officer

Commissioner of Patents and Trademarks